US00PP10426P

United States Patent [19]

Danziger

[11] Patent Number: Plant 10,426

[45] Date of Patent: Jun. 2, 1998

[54] PETUNIA PLANT NAME 'CASCHAMP'

[75] Inventor: Gabriel Danziger, Nir Tzvi, Israel

[73] Assignee: Danziger - "Dan" Flower Farm, Post Beit Dagan, Israel

[21] Appl. No.: 660,171

[22] Filed: Jun. 3, 1996

[51] Int. Cl.[6] ..... A01H 5/00

[52] U.S. Cl. ..... Plt./68.1

[58] Field of Search ..... Plt./68.1

[56] References Cited

U.S. PATENT DOCUMENTS

| | | | |
|---|---|---|---|
| P.P. 6,899 | 7/1989 | Tsuda et al. | Plt./68.1 |
| P.P. 6,914 | 7/1989 | Tsuda et al. | Plt./68.1 |
| P.P. 6,915 | 7/1989 | Tsuda et al. | Plt./68.1 |
| P.P. 8,889 | 9/1994 | Danziger | Plt./68.1 |
| P.P. 8,914 | 9/1994 | Danziger | Plt./68.1 |
| P.P. 8,915 | 9/1994 | Danziger | Plt./68.1 |
| P.P. 8,934 | 10/1994 | Danziger | Plt./68.1 |
| P.P. 9,322 | 10/1995 | Tachibana et al. | Plt./68.1 |
| P.P. 9,341 | 10/1995 | Tachibana et al. | Plt./68.1 |
| P.P. 9,342 | 10/1995 | Sakazaki et al. | Plt./68.1 |
| P.P. 9,408 | 12/1995 | Rother | Plt./68.1 |
| P.P. 9,556 | 5/1996 | Tachibana et al. | Plt./68.1 |
| P.P. 9,577 | 5/1996 | Suzuki et al. | Plt./68.1 |

*Primary Examiner*—James R. Feyrer
*Assistant Examiner*—Kent L. Bell

[57] ABSTRACT

The petunia cultivar 'Caschamp' is particularly characterized by vigorous growth and abundant flower production under diverse conditions including heat as well as moderate winter temperatures; a flower with an upper side that is brilliant pink with a dark purple center and a lower side that is light purple with dark veins and a long garden season in which growth and flowering continues from early spring until late winter.

1 Drawing Sheet

The present invention comprises a new and distinct cultivar of petunia known by the cultivar name 'Caschamp'. 'Caschamp' originated from a hybridization made by the inventor in a controlled breeding program in Mishmar Hashiva, Israel in 1995. The female parent was a proprietary line designated CV 75 and the male parent was a proprietary line designated CV 102. 'Caschamp' was discovered and selected as one flowering plant within the progeny of the stated cross by the inventor Gaby Danziger in May 1995 in a controlled environment in Mishmar Hashiva.

The first act of asexual reproduction of 'Caschamp' was accomplished when vegetative cuttings were taken from the initial selection in June 1995 in a controlled environment in Mishmar Hashiva by the inventor. Horticultural examination of selected units initiated in September 1995 has demonstrated that the combination of characteristics as herein disclosed for 'Caschamp' are firmly fixed and are retained through successive generations of asexual reproduction.

'Caschamp' has not been observed under all possible environmental conditions. The phenotype may vary somewhat with variations in environment such as temperature, light intensity and day length without any variation in genotype. The following observations, measurements and comparisons describe the plants grown in Mishmar Hashiva under greenhouse conditions which approximate those generally used in commercial practice.

The following traits have been repeatedly observed and are determined to be basic characteristics of 'Caschamp' which in combination distinguish this petunia as a new and distinct cultivar:

1. Excellent garden performance under full sunlight and the variety is also suitable for indoor usage.
2. Good tolerance to diverse weather conditions and vigorous growth in hot temperatures and during moderate winter. The plant recovers nicely after heavy rains.
3. Vigorous growth with trailing dark green (RHS 146A) foliage.
4. Abundant production of luminous purple (RHS 74B) flowers that are medium in size.
5. Long garden season maintaining growth and flowering from early spring until late winter.
6. No particular susceptibility to common diseases of petunia.

Of the many commercial cultivars known to the inventor the most similar in comparison to 'Caschamp' is 'Revolution'. In comparison to 'Revolution', the cultivar 'Caschamp' has better garden performance due to its vigorous growth and distinctive flower color. Unlike 'Revolution', the cultivar 'Caschamp' maintains flowering during moderate winter.

The accompanying photographic drawing shows typical flower and foliage characteristics of 'Caschamp', with the color being as true as possible with illustrations of this type.

Sheet 1 is a side view of a typical specimen of the variety 'Caschamp' showing the amount abundant flower production, distinctive flower color and plant form of this variety.

In the following description, color references are made to The Royal Horticultural Society Color Chart. The color values were determined between 10:00–12:00 a.m. on Jan. 28, 1996 under full sunlight at Mishmar Hashiva.

Classification:

*Botanical.*—Petunia hybrid.

*Commercial.*—Petunia cultivar 'Caschamp'.

Plant:

*Growth habit.*—Trailing, vigorous, fast growing.

*Plant height.*—8–10 inches.

*Spreading area.*—30 inches.

*Blooming period.*—From early spring until late winter.

Stem:

*Thickness.*—2–3 mm.

*Color.*—Dark green (RHS 146A) with purple (RHS 77A) coloration during low temperature.

*Pubescence.*—Yes.

*Branching.*—Free.

*Length of internode.*—10–20 mm.

Leaf:

*Arrangement on stem.*—Alternate.

*Shape.*—Oblong with a simple leaf that is ovate.

*Size.*—Length: 95 mm. Width: 49 mm.

*Thickness.*—0.2 mm.

*Color.*—Dark green (RHS 146A).

*Pubescence.*—Yes.

Flower:

*Orientation at opening.*—Upright.

*Type.*—Single.

*Shape.*—Regular and rounded with a corolla that is united with 5 lobes and a long straight tube.

*Diameter.*—5–60 mm.

*Color.*—Upper side: Brilliant purple (RHS 74B) with dark purple (RHS 86A) center. Lower side: Light purple (RHS 72B) with dark purple (71A) veins. As the flower matures the color intensity on the upper and lower surfaces fades a little.

*Peduncle.*—Length: 20–25 mm. Color: Green (RHS 146A).

*Reproductive organs.*—Pistil: Number: 1. Color: Green (RHS 138C). Stamens: Number 5. Anther: Blue (RHS 98C). Filament: Green (RHS 138D).

Disease resistance:

Not particularly susceptible to common petunia diseases.

I claim:

1. A new cultivar of petunia plant named 'Caschamp' as shown and described herein.

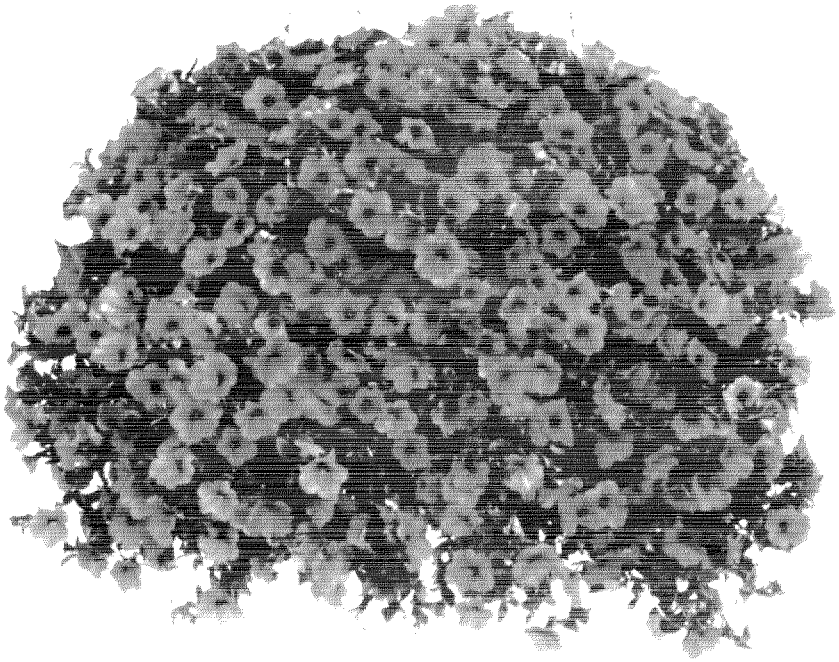

* * * * *